United States Patent [19]
Hann et al.

[11] Patent Number: 5,268,490
[45] Date of Patent: Dec. 7, 1993

[54] BENZOFURANONES

[75] Inventors: Richard A. Hann, Ipswich; Nigel Hall, Bury; Gary W. Morrison, London; Dean Thetford, Failsworth, all of England

[73] Assignee: Imperial Chemical Industries PLC, London, United Kingdom

[21] Appl. No.: 955,021

[22] Filed: Oct. 1, 1992

[30] Foreign Application Priority Data

Oct. 1, 1991 [GB] United Kingdom ............... 9120785
Oct. 1, 1991 [GB] United Kingdom ............... 9120786

[51] Int. Cl.$^5$ ........................................... C07D 307/83
[52] U.S. Cl. ...................................... 549/304; 549/305
[58] Field of Search ................................ 549/304, 305

[56] References Cited

U.S. PATENT DOCUMENTS 4,704,458 11/1987 Tokeda et al. ................. 549/305

FOREIGN PATENT DOCUMENTS 0363034 4/1990 European Pat. Off. .

Primary Examiner—C. Warren Ivy
Assistant Examiner—A. A. Owens
Attorney, Agent, or Firm—Cushman, Darby & Cushman

[57] ABSTRACT

A benzofuranone of the Formula (1):

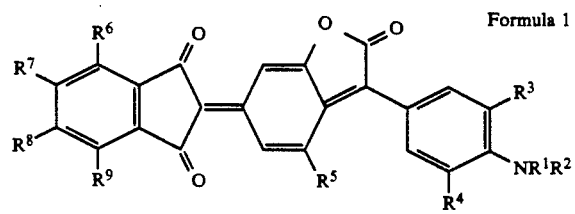

wherein:

$R^1$ and $R^2$ are each independently —H or optionally substituted $C_{1-20}$-alkyl;

$R^3$ and $R^4$ are each independently —H or optionally substituted $C_{1-6}$-alkyl;

$R^5$ is selected from —H, —CN, —COOR$^{10}$ and —COR$^{10}$, in which $R^{10}$ is —H or $C_{1-6}$-alkyl;

$R^6$, $R^7$, $R^8$ and $R^9$ are each independently selected from —H, —NR$^1$R$^2$, —NO$_2$, halogen, optionally substituted $C_{1-6}$-alkyl and optionally substituted $C_{1-6}$-alkoxy.

3 Claims, No Drawings

BENZOFURANONES

This specification describes an invention relating to novel benzofuranones, to methods for their preparation, to their use in dye diffusion thermal transfer printing (DDTTP), to a transfer sheet coated with a benzofuranone or a mixture of benzofuranones and to a transfer printing process in which the benzofuranone is transferred from the transfer sheet to a receiver sheet by the application of heat, and to their use as infra-red absorbers.

According to the present invention there is provided a benzofuranone of the Formula (1):

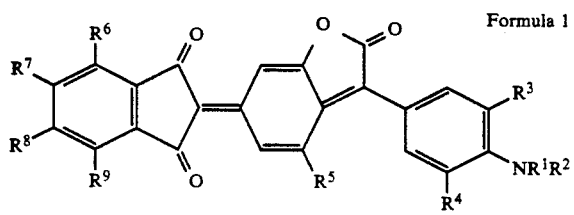

Formula 1 wherein:

$R^1$ and $R^2$ are each independently —H or optionally substituted $C_{1-20}$-alkyl;

$R^3$ and $R^4$ are each independently —H or optionally substituted $C_{1-6}$-alkyl;

$R^5$ is selected from —H, —CN, —COOR$^{10}$ and —COR$^{10}$, in which $R^{10}$ is —H or $C_{1-6}$-alkyl; and $R^6$, $R^7$, $R^8$ and $R^9$ are each independently selected from —H, —NR$^1$R$^2$, —NO$_2$, halogen, optionally substituted $C_{1-6}$-alkyl and optionally substituted $C_{1-6}$-alkoxy.

In compounds of Formula (1) groups represented by $R^3$ and $R^4$ are preferably —H or $C_{1-4}$-alkyl, and more preferably —H, —CH$_3$ or —C$_2$H$_5$.

Where any one of the groups represented by $R^1$ to $R^9$ is optionally substituted, it preferably carries from 1 to 4, and especially 1 or 2, substituents, selected from $C_{1-6}$-alkyl, $C_{1-6}$-alkoxy, nitro, chloro, fluoro, hydroxy, cyano, carboxy, phenyl and cyclohexyl.

It is preferred that $R^1$ and $R^2$ are each independently —H or $C_{1-6}$-alkyl, more preferably —H or $C_{1-12}$-alkyl and especially —H or $C_{1-8}$-alkyl. Where any one of the groups represented by $R^1$ to $R^{10}$ is alkyl it may be a straight or a branched chain alkyl group.

Where any of the groups represented by $R^6$, $R^7$, $R^8$ and $R^9$ are halogen, the halogen is preferably —F, —Cl, —Br.

It is preferred that $R^5$, $R^6$, $R^7$, $R^8$ and $R^9$ are all —H.

According to a further feature of the present invention there is provided a process for the preparation of a benzofuranone of Formula (1) by reacting a compound of the Formula (2):

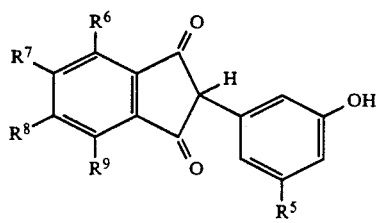

Formula 2 with a compound of the Formula (3):

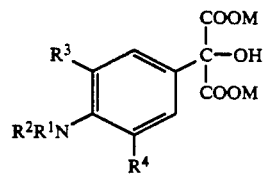

Formula 3 wherein $R^1$ to $R^9$ are as hereinbefore defined; and

M is —H or metal.

In compounds of Formula (3) it is preferred that M is H or is an alkali metal such as sodium or potassium.

The present process may be performed by heating the reactants in a liquid medium, preferably in an acidic medium, more preferably in an organic acid and especially in an alkane carboxylic acid such as acetic acid, propionic acid or butyric acid.

The process is preferably performed at a temperature from 50° to 200° C., more preferably at 100° to 150° C. and conveniently at the boiling point of the liquid medium. The process may be optionally performed at elevated pressure. The reaction mixture may contain additional liquid media such as solvents which do not interfere with the reaction. The reaction is preferably continued until all the starting materials are consumed which may take up to 10 hours. Product may be isolated from the reaction mixture by any convenient means for example the acid and any additional solvents may be evaporated to leave a solid which may be purified by crystallisation from an organic solvent such as methanol.

According to a further feature of the present invention there is provided a compound of the Formula (2):

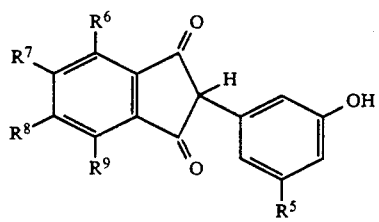

Formula 2 wherein $R^5$ to $R^9$ are as hereinbefore defined, except for the compound in which $R^5$ to $R^9$ are all —H.

The compound of Formula (2) may be prepared by reaction of a compound of the Formula (4):

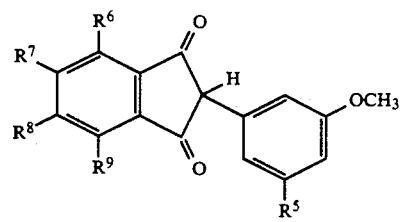

Formula 4 with hydroiodic acid wherein $R^5$ to $R^9$ are as hereinbefore defined.

The compound of Formula (4) may be prepared by known methods, such as the appropriately substituted reaction of a phthalide with an aryl acetic acid followed by rearrangement in sodium methoxide solution to form the compound of Formula (4). Further details of this reaction are provided in Journal of Medical Chemistry, 11, 342, (1968). Alternatively, the compound of Formula (4) may be prepared by reaction of a benzofuranone of Formula (5):

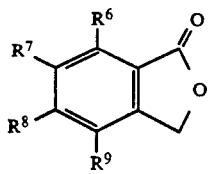

Formula 5 with a substituted 3-methoxybenzaldehyde in accordance with the procedures described in Journal of Organic Chemistry 25, 180 (1960), Journal of Medical Chemistry 28, 1591 (1985), and Journal of Medical Chemistry 11, 342 (1968). Benzofuranones of Formula (5) may be prepared in accordance with the procedures described in Heterocyclic Compounds A Vol 29, 251 (1974).

Compounds of Formula (3) may be prepared by known methods, such as the reaction of an aniline with alloxan in the presence of an acid followed by reaction with an alkali metal hydroxide. These reactions are further described in British patent No 1088.

The compounds of the present invention are dyes which absorb radiation predominantly in the infra-red region of the spectrum and are useful in providing patterns which are detectable by suitable infra-red detectors and are thus machine readable. Such patterns may be created using dye diffusion thermal transfer printing (DDTTP) in which a transfer sheet is formed by applying a coating comprising a heat-transferable dye to a thin (usually <20 micron) substrate having a smooth plain surface (usually as an ink also containing a polymeric or resinous binder to bind the dye to the substrate) in the form of a continuous even film over the entire printing area of the transfer sheet. Dye is then selectively transferred from the transfer sheet by placing it in contact with a material having a smooth surface with an affinity for the dye, hereinafter called the receiver sheet, and selectively heating discrete areas of the reverse side of the transfer sheet for periods from about 1 to 20 milliseconds (msec) and temperatures up to 300° C., in accordance with a pattern information signal whereby dye from the selectively heated regions of the transfer sheet is transferred to the receiver sheet and forms a pattern thereon in accordance with the pattern in which heat is applied to the transfer sheet. The shape of the pattern is determined by the number and location of the discrete areas which are subjected to heating and the depth of shade in any discrete area is determined by the period of time for which it is heated and the temperature reached.

Heating is generally, though not necessarily, effected by a line of heating elements, over which the receiver and transfer sheet are passed together. Each element is approximately square in overall shape, although the element may optionally be split down the centre and may be resistively heated by an electric current passed through it from adjacent circuitry. Each element normally corresponds to an element of image information and can be separately heated to 300° C. to 400° C. in less than 20 msec and preferably in less than 10 msec, usually by an electric pulse in response to a pattern information signal. During the heating period the temperature of an element will rise from about 70° C. to 300°–400° C. over about 5–8 msec. With increase in temperature and time more dye will diffuse from the transfer sheet to the receiver sheet and thus the amount of dye transferred onto, and the depth of shade at, any discrete area on the receiver sheet will depend on the period for which an element is heated while it is in contact with the reverse side of the transfer sheet.

As heat is applied through individually energised elements for very short periods of time the process is selective in terms of location and quantity of dye transferred and the transferred dye remains close to the surface of the receiver sheet.

As an alternative, heating may be effected using a light source in a light-induced thermal transfer (LITT) printer where the light source can be focused, in response to an electronic pattern information signal, on each area of the transfer sheet to be heated. The heat for effecting transfer of the dye from the transfer sheet is generated in the dyesheet which contains an absorber for the inducing light. The absorber is selected according to the light source used and enhances the conversion of light to thermal energy, at a point at which the light is incident, in order to provide sufficient heat to transfer the dye at that point to the corresponding position on the receiver sheet. The inducing light usually has a narrow waveband and may be in the visible, infra-red or ultra violet regions although infra-red emitting lasers are particularly suitable.

There are significant distinctions between the mechanism involved in the thermally induced transfer of disperse dyes from transfer sheets onto uneven textile materials which involves sublimation of the dye and the present DDTTP onto smooth polymeric surfaces which involves melt diffusion and it has been found that dyes which are suitable for the former process are not necessarily suitable for the latter.

In DDTTP it is important that the surfaces of the transfer sheet and receiver sheet are even so that good contact can be achieved between the printed surface of the transfer sheet and the receiving surface of the receiver sheet over the entire printing area because it is believed that the dye is transferred substantially by diffusion in the molten state in condensed phases. It has been found that any defect or speck of dust which prevents good contact over any part of the printing area will inhibit transfer and lead to an unprinted portion on the receiver sheet on the area where good contact is prevented, which can be considerably larger than the area of the speck or defect. The surfaces of the substrate of the transfer and receiver sheets are usually a smooth polymeric film, especially of a polyester, which has some affinity for the dye.

Important criteria in the selection of a dye for DDTTP are its thermal properties, fastness properties, such as light fastness, and facility for transfer by melt diffusion into the substrate in the DDTTP process. For suitable performance the dye or dye mixture should transfer evenly and rapidly, in proportion to the heat applied to the transfer sheet so that the amount transferred to the receiver sheet is proportional to the heat applied. After transfer the dye should preferably not migrate or crystallise and should have excellent fastness to light, heat, rubbing, especially rubbing with a oily or greasy object, e.g. a human finger, such as would be encountered in normal handling of of the printed receiver sheet. As the dye should be sufficiently mobile to migrate from the transfer sheet to the receiver sheet at the temperatures employed, 100°-400° C., in the short time-scale, generally <20 msec, it is preferably free from ionic and/or water-solubilising groups, and is thus not readily soluble in aqueous or water-miscible media, such as water and ethanol. Many potentially suitable dyes are also not readily soluble in the solvents which are commonly used in, and thus acceptable to, the printing industry; for example, alcohols such as i-propanol, ketones such as methyl ethyl ketone (MEK), methyl i-butyl ketone (MIBK) and cyclohexanone, ethers such as tetrahydrofuran and aromatic hydrocarbons such as toluene. The dye can be applied as a dispersion in a suitable medium or as a solution in a suitable solvent to the substrate from a solution. In order to achieve the potential for a high optical density (OD) on the receiver sheet it is desirable that the dye should be readily soluble or readily dispersable in the ink medium. It is also important that a dye which has been applied to a transfer sheet from a solution should be resistant to crystallisation so that it remains as an amorphous layer on the transfer sheet for a considerable time. Crystallisation not only produces defects which prevent good contact between the transfer receiver sheet but gives rise to uneven prints.

The following combination of properties is highly desirable for a dye which is to be used in DDTTP:

Ideal spectral characteristics (narrow absorption curve)
Correct thermochemical properties (high thermal stability and efficient transferability with heat).
High optical densities on printing.
Good solubility in solvents acceptable to printing industry: this is desirable to produce solution coated dye-sheets alternatively good dispersion in acceptable media is desirable to produce dispersion coated dye-sheets.
Stable dyesheets (resistant to dye migration or crystallisation).
Stable printed images on the receiver sheet (resistant to heat, migration, crystallisation, grease, rubbing and light).

Although DDTTP is generally used for printing visually detectable images on a suitable substrate, if suitable compounds such as those of the present invention, having absorption in the infra-red region of the spectrum, are used in place of dyes which absorb radiation in the visible region of the electromagnetic spectrum, it is possible to produce patterns which are detectable by suitable infra-red detectors and therefore are machine readable.

According to a further feature of the present invention there is provided a thermal transfer printing sheet comprising a substrate having a coating comprising a benzofuranone of Formula (1):

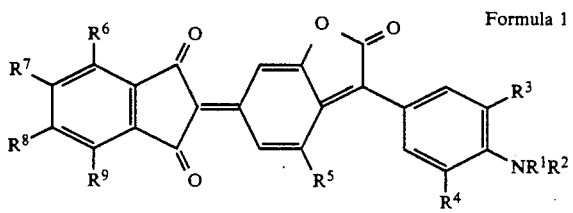

Formula 1 wherein:

$R^1$, $R^2$, $R^3$, $R^4$, $R^5$, $R^6$, $R^7$, $R^8$ and $R^9$ are as hereinbefore defined.

Groups represented by $R^1$ and $R^2$ are preferably —H or $C_{1-16}$-alkyl, more preferably —H or $C_{1-12}$-alkyl and especially —H or $C_{1-8}$-alkyl.

Groups represented by $R^3$ and $R^4$ are preferably —H or $C_{1-4}$-alkyl and more preferably —H, —$CH_3$ or —$C_2H_5$.

Where any one of the groups represented by $R^6$ to $R^9$ is halogen, the halogen is preferably —F, —Cl or —Br.

Suitable substituents for the alkyl groups represented by $R^1$ to $R^9$ are preferably selected from —OH, —CN, —$C_{1-6}$-alkyl, —$OC_{1-6}$-alkyl, —Cl, —F, —Br, —$NH_2$, —$NHC_{1-6}$-alkyl and —$N(C_{1-6}$-alkyl$)_2$.

Where any one of the groups represented by $R^1$ and $R^{10}$ is alkyl it may be straight or branched chain alkyl.

Specific examples of suitable dyes of Formula (1) are shown in Table 1.

TABLE 1

| Dye | $R^1$ | $R^2$ | $R^3$ | $R^4$ |
|---|---|---|---|---|
| 1 | —$(CH_2)_5CH_3$ | —$(CH_2)_5CH_3$ | —H | —H |
| 2 | —$(CH_2)_7CH_3$ | —$(CH_2)_7CH_3$ | —H | —H |
| 3 | —H | —H | —$CH_3$ | —$CH_3$ |
| 4 | —$CH_3$ | —$CH_3$ | —H | —H |
| 5 | —$C_2H_5$ | —$C_2H_5$ | —H | —H |
| 6 | —$(CH_2)_3CH_3$ | —$(CH_2)_3CH_3$ | —H | —H |
| 7 | —$(CH_2)_{11}CH_3$ | —$(CH_2)_{11}CH_3$ | —H | —H |
| 8 | —$(CH_2)_{15}CH_3$ | —$(CH_2)_{15}CH_3$ | —H | —H |

The dyes of Formula (1) absorb electromagnetic radiation in the region wavelength from 650 nm to 900 nm, give good densities (OD) and may be used as infra-red absorbers in security printing and in bar-coding.

The Coating

The coating suitably comprises a binder together with a dye of Formula (1). The ratio of binder to dye is preferably at least 0.7:1 and more preferably from 1:1 to 4:1 and especially preferably 1:1 to 2:1 in order to provide good adhesion between the dye and the substrate and inhibit migration of the dye during storage.

The coating may also contain other additives, such as curing agents, preservatives, etc., these and other ingredients being described more fully in EP 133011A, EP 133012A and EP 111004A.

The Binder

The binder may be any resinous or polymeric material suitable for binding the dye to the substrate which has acceptable solubility in the ink medium, i.e. the medium in which the dye and binder are applied to the transfer sheet. It is preferred however, that the dye is soluble in the binder so that it can exist as a solid solution in the binder on the transfer sheet. In this form it is generally more resistant to migration and crystallisation during storage. Examples of binders include cellulose derivatives, such as ethylhydroxyethylcellulose (EHEC), hydroxypropylcellulose (HPC), ethylcellulose, methylcellulose, cellulose acetate and cellulose acetate butyrate; carbohydrate derivatives, such as starch; alginic acid derivatives; alkyd resins; vinyl resins and derivatives, such as polyvinyl alcohol, polyvinyl acetate, polyvinyl butyral, polyvinyl acetoacetal and polyvinyl pyrrolidone; polymers and copolymers derived from acrylates and acrylate derivatives, such as polyacrylic acid, polymethyl methacrylate and styrene-acrylate copolymers, styrene derivatives such as polystyrene, polyester resins, polyamide resins, such as melamines; polyurea and polyurethane resins; organosilicones, such as polysiloxanes, epoxy resins and natural resins, such as gum tragacanth and gum arabic. Mixtures of two or more of the above resins may also be used, mixtures preferably comprise a vinyl resin or derivative and a cellulose derivative, more preferably the mixture comprises polyvinyl butyral and ethylcellulose. It is also preferred to use a binder which is soluble in one of the above-mentioned commercially acceptable organic solvents. Preferred binders of this type are EHEC, particularly the low and extra-low viscosity grades, and ethyl cellulose.

The benzofuranones of Formula (1) have good thermal properties giving rise to even prints on the receiver sheet, whose density is accurately proportional to the quantity of applied heat so that a true grey scale can be attained.

The benzofuranones of Formula (1) also have strong absorbance properties and are soluble in a wide range of solvents, especially those solvents which are widely used and accepted in the printing industry, for example, alkanols, such as i-propanol and butanol; aromatic hydrocarbons, such as toluene, ethers, such as tetrahydrofuran and ketones such as MEK, MIBK and cyclohexanone. Alternatively the benzofuranones may be dispersed by high shear mixing in suitable media such as water, in the presence of dispersing agents. This produces inks (solvent plus benzofuranones and binder) which are stable and allow production of solution or dispersion coated transfer. The latter are stable, being resistant to benzofuranone crystallisation or migration of the benzofuranones during prolonged storage.

The combination of strong absorbance properties and good solubility in the preferred solvents allows the achievement of a high density print of the benzofuranone of Formula (1) on the receiver sheet. The printed receiver sheets according to the present invention have strong prints which are fast to both light and heat.

The Substrate

The substrate may be any sheet material preferably having at least one smooth even surface and capable of withstanding the temperatures involved in DDTTP, i.e. up to 400° C. for periods up to 20 msec, yet thin enough to transmit heat applied on one side through to the dyes on the other side to effect transfer of the dye onto a receiver sheet within such short periods. Examples of suitable materials are polymers, especially polyester, polyacrylate, polyamide, cellulosic and polyalkylene films, metallised forms thereof, including copolymer and laminated films, especially laminates incorporating a smooth even polyester receptor layer on which the dye is deposited. Thin ( < 20 micron) high quality paper of even thickness and having a smooth coated surface, such as capacitor paper, is also suitable. A laminated substrate preferably comprises a backcoat, on the opposite side of the laminate from the receptor layer, which, in the printing process, holds the molten mass together, such as a thermosetting resin, e.g. a silicone, acrylate or polyurethane resin, to separate the heat source from the polyester and prevent melting of the latter during the DDTTP operation. The thickness of the substrate depends to some extent upon its thermal conductivity but it is preferably less than 20 $\mu$m and more preferably less than 10 $\mu$m.

The DDTTP Process

According to a further feature of the present invention there is provided a dye diffusion thermal transfer printing process which comprises contacting a transfer sheet comprising a coating comprising a dye of Formula (1) with a receiver sheet, so that the coating is in contact with the receiver sheet and selectively applying heat to discrete areas on the reverse side of the transfer sheet whereby the dye on the opposite side of the sheet to the heated areas is transferred to the receiver sheet.

Heating in the selected areas can be effected by contact with heating elements, which can be heated to 200°–450° C., preferably 200°–400° C., over periods of 2 to 10 msec, whereby the dye mixture may be heated to 150°–300° C., depending on the time of exposure, and thereby caused to transfer, substantially by diffusion, from the transfer sheet to the receiver sheet. Good contact between coating and receiver sheet at the point of application is essential to effect transfer. The density of the printed image is related to the time period for which the transfer sheet is heated.

The Receiver Sheet

The receiver sheet conveniently comprises a polyester sheet material, which may be a transparent or a white polyester film, preferably of polyethylene terephthalate (PET). In thermal transfer printing, the time period is so short that the dye does not penetrate the PET and the substrate is preferably provided with a receptive layer, on the side to which the dye is applied, into which the dye mixture more readily diffuses to form a stable image. Such a receptive layer, which may be applied by co-extrusion or solution coating techniques, may comprise a thin layer of a modified polyester or a different polymeric material which is more permeable to the dye than the PET substrate. While the nature of the receptive layer will affect to some extent the depth of shade and quality of the print obtained it has been found that the dyes of Formula (1) give particularly strong and good quality prints (e.g. fast to light, heat and storage) on any specific transfer or receiver sheet. The design of receiver and transfer sheets is discussed further in EP 133,011 and EP 133012.

The transfer sheets of the present invention may be used to produce laser readable bar codes and in security printing applications.

The compounds of the present invention are also useful as infra-red absorbers in applications such as optical data storage and security printing.

The invention is further illustrated by the following Examples in which all parts and percentages are by weight unless otherwise indicated.

Example 1

Preparation of 6-(1,3-dioxoindan-2-ylidene)-2-oxo-3-(4-amino-3,5-dimethylphenyl) -2,6-dihydrobenzofuran (i) Alloxan (50 parts) was added to a stirred solution of 2,6-dimethylaniline (37.6 parts) in glacial acetic acid (25 parts), ethanol (117 parts) and water (117 parts) at 25° C. The mixture was heated to 80° C. and stirred for 1½ hours. The reaction mixture was cooled to 10° C. and the precipitated solid was isolated by filtration, washed with water and dried at 70° C. to yield 2,6-dimethylaniline-4- alloxan (74.4 parts, 91%), m.pt. >250° C.

(ii) The 2,6-dimethyl-4-alloxan (54 parts) from (i) above, potassium hydroxide (205 parts) and water (600 parts) were stirred and refluxed for 8 hours. Water was evaporated until a solid started to precipitate and the reaction mixture was cooled to 25° C. Ethanol (74

OP; 500 parts) was added and the precipitated solid was isolated by filtration, washed with ethanol (74 OP) and dried at 60° C. to yield 4-amino-3,5-dimethylphenyl tartronic acid dipotassium salt (49.2 parts, 35%), m.pt. >250° C.

(iii) Sodium (18.9 parts) was dissolved in absolute ethanol (380 parts) with stirring and was cooled to 20° C. and benzofuranone (100 parts) and 3-methoxybenzaldehyde were added. The reaction mixture was stirred under reflux for 15 minutes and cooled to 20° C. over 1 hour. The reaction mixture was poured into water (900 parts) and the ethanol was removed by evaporation under reduced pressure. Hydrochloric acid was added to the solution until acid and the aqueous phase was decanted to leave a red gum. The gum was dissolved in hot acetic acid (300 parts) and the solution was cooled to 20° C. and a solid was precipitated. The solid was isolated by filtration, washed with ethanol (74 OP) and dried to give 2-(3-methoxyphenyl)-1,3-indandione (55.8 parts) m.pt. 142°-144° C.

(iv) Hydroiodic acid (50%, 205 parts) was added to 2-(3-methoxyphenyl)-1,3-indandione (67.1 parts) and the mixture was stirred under reflux for 10 minutes. By-product methyl iodide was removed by distillation and the solution was cooled to 20° C. The aqueous layer was decanted to leave a red oil. The oil was dissolved in chloroform (250 parts), washed with water (100 parts), separated and dried over anhydrous magnesium sulphate. The chloroform was removed by evaporation under reduced pressure to leave an orange solid. The solid was crystallised from toluene (1800 parts) to yield 2-(3-hydroxyphenyl)-1,3-indandione (30.6 parts), m.pt. 139°-141° C.

(v) 4-Amino-3,5-dimethylphenyltartronic acid (2.1 parts), 2-(3-hydroxyphenyl)-1,3-indandione (1.3 parts) and glacial acetic acid (125 parts) were stirred under reflux for 2 hours. The reaction mixture was cooled to 20° C. and the precipitated solid was recovered by filtration, washed with methanol and dried to give 6-(1,3-dioxoindan-2-ylidene)-2-oxo-3-(4-amino-3,5-dimethylphenyl)-2,6-dihydrobenzofuran (0.9 parts, 38%), m.pt. >250° C. λmax (CH$_2$Cl$_2$)=656nm.

Example 2

Preparation of
6-(1,3-dioxoindan-2-ylidene)-2-oxo-3-(4-N-ethylamino-3-methylphenyl)-2,6-dihydrobenzofuran (i) The procedure of Example 1(i) was repeated except that the 2,6-dimethylaniline was replaced by N-ethyl-3-methylaniline (15 parts) to give N-ethyl-3-methylaniline-4-alloxan (21 parts, 68%).

(ii) The procedure of Example 1(ii) was repeated except that the 2,6-dimethylaniline-4-alloxan was replaced by N-ethyl-3-methylaniline-4-alloxan (21 parts) to give N-ethylamino-3-methylphenyl tartronic acid dipotassium salt (27 parts, 100%).

(iii) The procedure of Example 1(v) was repeated except that the 4-amino-3,5-dimethylphenyl tartronic acid was replaced by N-ethylamino-3-methylphenyl tartronic acid (7.5 parts) and 3.8 parts instead of 1.3 parts of 2-(3-hydroxyphenyl)-1,3-indandione were used.

6-(1,3-Dioxoindan-2-ylidene)-2-oxo-3-(4-N-ethylamino-3-methylphenyl)-2,6-dihydrobenzofuran (1.9 parts, 23%), m.pt. >250° C., λmax (CH$_2$Cl$_2$)=706nm was obtained.

Example 3

Preparation of
6-(1,3-dioxoindan-2-ylidene)-2-oxo-3-(4-N,N-diethylamino-3,5-dimethylphenyl)-2,6-dihydrobenzofuran (i) The procedure of Example 1(i) was repeated except that the 2,6-dimethylaniline was replaced by N,N-diethylaniline (46.6 parts) to give N,N-diethylaniline-4-alloxan (64.3 parts, 71 %) m.pt. 190°-192° C.

(ii) The procedure of Example 1(ii) was repeated except that the 2,6-dimethylaniline-4-alloxan was replaced by N,N-diethylaniline-4-alloxan (100 parts), 453.6 parts instead of 205 parts of potassium hydroxide and 760 parts instead of 600 parts of water were used. N,N-diethylaminophenyl tartronic acid (39.5 parts, 34 %) m.pt. >250° C. was obtained as a white crystalline solid.

(iii) The procedure of Example 1(v) was repeated except that the 4-amino-3,5-dimethylphenyl tartronic acid was replaced by N,N-diethylaminophenyltartronic acid (39.2 parts), 18.1 parts instead of 1.3 parts of 2-(3-hydroxyphenyl)-1,3-indandione and 600 parts instead of 125 parts of glacial acetic acid were used. 6-(1,3-Dioxoindan-2-ylidene)-2-oxo-3-(4-N,N-diethylaminophenyl)-2,6-dihydrobenzofuran (6.5 parts, 20%), m.pt. >250° C., λmax (CH$_2$Cl$_2$)=757nm was obtained.

Example 4

Preparation of
6-(1.3-dioxoindan-2-ylidene)-2-oxo-3-(4-N,N-dibutylaminophenyl)-2,6-dihydrobenzofuran (i) The procedure of Example 1(i) was repeated except that the 2,6-dimethylaniline was replaced by N,N-dibutylaniline (13.5 parts), 14 parts instead of 50 parts of alloxan, 7.4 parts instead of 25 parts of acetic acid, 34 parts instead of 117 parts of ethanol and 34 parts instead of 117 parts of water to give N,N-dibutylaniline-4-alloxan (24.3 parts, 70.7 %) m.pt. 227°-230° C.

(ii) The procedure of Example 1(ii) was repeated except that the 2,6-dimethylaniline-4-alloxan was replaced by N,N-dibutylaniline-4-alloxan (24 parts) to give N,N-dibutylaminophenyl tartronic acid dipotassium salt (8.7 parts, 34%), m.pt. 250° C.

(iii) The procedure of Example 1(v) was repeated except that the 4-amino-3,5-dimethylphenyl tartronic acid was replaced by 4-N,N-dibutylaminophenyl tartronic acid (30 parts), 12.5 parts instead of 1.3 parts of 2-(3-hydroxyphenyl)-1,3-indandione and 350 parts instead of 125 parts of glacial acetic acid were used. 6-(1,3-Dioxoindan-2-ylidene)-2-oxo-3-(4-N,N-dibutylaminophenyl)-2,6-dihydrobenzofuran (7.6 parts, 17%), m.pt. 210°-212° C., λmax (CH$_2$Cl$_2$)=774nm was obtained.

Example 5

Preparation of
6-(1,3-dioxoindan-2-ylidene)-2-oxo-3-(4-N,N-dihexylaminophenyl)-2,6-dihydrobenzofuran (i) The procedure of Example 1(i) was repeated except that the 2,6-dimethylaniline was replaced by N,N-dihexylaniline (60 parts) to give N,N-dihexylaniline-4-alloxan (69.6 parts, 72 %) m.pt. °C.

(ii) The procedure of Example 1(ii) was repeated except that the 2,6-dimethyl-4-alloxan was replaced by N,N-dihexylaniline-4-alloxan (0.9 parts) to give N,N- dihexyl- aminophenyl tartronic acid dipotassium salt (1.0 parts, 87%).

(iii) The procedure of Example 1(v) was repeated except that the 4-amino-3,5-dimethylphenyl tartronic acid was replaced by 4-N,N-dihexylaminophenyltartronic acid (1 part), 1.5 parts instead of 1.3 parts of 2-(3-hydroxyphenyl)-1,3-indandione and 30 parts instead of 125 parts of glacial acetic were used.

6-(1,3-Dioxoindan-2-ylidene)-2-oxo-3-(4-N,N-dihexylaminonyl)-2,6-dihydrobenzofuran (0.3 parts, 13%), m.pt. 189°–192° C., λmax (CH$_2$Cl$_2$)=772nm was obtained.

Example 6

Preparation of 6-(1,3-dioxoindan-2-ylidene)-2-oxo-3-(4-N,N-dioctylaminophenyl)-2,6-dihydrobenzofuran (i) The procedure of Example 1(i) was repeated except that the 2,6-dimethylaniline was replaced by N,N-dioctylaniline (69 parts) to give N,N-dioctylaniline-4-alloxan (48.5 parts, 48%) as a yellow waxy solid.

(ii) The procedure of Example 1(ii) was repeated except that the 2,6-dimethyl-4-alloxan was replaced by N,N-dioctylaniline-4-alloxan (48.5 parts) to give N,N-dioctyl-aminophenyl tartronic acid dipotassium salt (16.7 parts, 31%).

(iii) The procedure of Example 1(v) was repeated except that the 4-amino-3,5-dimethylphenyltartronic acid was replaced by 4-N,N-dioctylaminophenyltartronic acid (16.7 parts), 7.3 parts instead of 1.3 parts of 2-(3-hydroxyphenyl)-1,3-indandione and 300 parts instead of 125 parts of glacial acetic acid were used.

6-(1,3-Dioxoindan-2-ylidene)-2-oxo-3-(4-N,N-dioctylaminophenyl)-2,6-dihydrobenzofuran (1.5 parts, 8%), m.pt. 152°–154° C., λmax (CH$_2$Cl$_2$)=774 nm was obtained.

Example 7

Preparation of 6-(1,3-dioxoindan-2-ylidene)-2-oxo-3-(4-N,N-didodecyl aminophepyl)-2,6-dihydrobenzofuran i) Alloxan monohydrate (24 parts), N,N-didodecylaniline (42.9 parts), glacial acetic acid (30 parts) and ethanol (120 parts) were stirred under reflux for 4 hours. The mixture was cooled to ambient temperature, diluted with water (200 parts) and cooled to 0° C. to precipitate a given solid which was collected by filtration and washed with water before drying at 60° C. to give N,N-didodecylaniline-4-alloxan (40 parts, 71%).

ii) The N,N-didodecylaniline-4-alloxan (38 parts), potassium hydroxide (33.6 parts) and ethanol (250 parts) were stirred under reflux for 8 hours before cooling to 0°–5° C. to precipitate a solid which was collected by filtration and dried under vacuum over phosphorus pentoxide to give N,N-didodecylaminophenyltartronic acid dipotassium salt (32.5 parts, 79%).

iii) N,N-Didodecylaminophenyltartronic acid dipotassium salt (18.2 parts), 2-(3-hydroxyphenyl)-I,3-indandione (7.3 parts) and glacial acetic acid 300 (parts) were stirred under reflux for 4 hours before cooling to ambient temperature to precipitate a green solid. The solid was isolated by filtration, washed with methanol and dried under vacuum over phosphorus pentoxide and calcium chloride to give 6-(1,3-dioxoindan-2-ylidene)-2-oxo-3-(N,N-didodecylaminophenyl)-2,6-dihydrobenzofuran (45 parts), 21%), m.pt. 155° C., λ$_{max}$(CH$_2$Cl$_2$)=776nm.

Example 8

Preparation of 6-(1,3-dioxoindan-2-ylidene)-2-oxo-3-(4-N,N-dihexadecyl aminophenyl)-2,6-dihydrobenzofuran i) The procedure of Example 7i) was followed except that N,N-dihexadecylaniline (54.1 parts) was used in place of the N,N-didodecylaniline, 40 parts instead of 30 parts of glacial acetic were used and the reaction mixture was stirred under reflux for 8 hours instead of 4 hours to give N,N-dihexadecylaniline-4-alloxan (67.5 parts, 99%).

ii) The procedure of Example 7ii) was followed except that N,N-dihexadecylaniline-4-alloxan (67 parts) was used instead of the N,N-didodecylaniline-4-alloxan, 56 parts instead of 33.6 parts of potassium hydroxide and 120 parts instead of 250 parts of ethanol were used to give N,N-dihexadecylaminophenyl tartronic acid dipotassium salt (70.8 parts, 98%).

iii) The procedure of Example 7iii) was followed except that N,N-dihexadecylaminophenyl tartronic acid dipotassium salt (22.8 parts) was used in place of the N,N-didodecylaminophenyl tartronic acid to give 6-(1,3-dioxoindan-2-ylidene)-2-oxo-3-(4-N,N-dihexadecylaminophenyl)-2,6-dihydrobenzofuran (6.2 parts, 25%), λ$_{max}$ (CH$_2$CH$_2$)=737 nm.

The performance of the compounds was evaluated in DDTTP as follows:

Ink 1

This was prepared by dissolving 0.15 parts of Dye 1 and 0.3 g polyvinyl butyral in 9.55 parts of tetrahydrofuran (THF).

Ink 2

This was prepared as described for Ink 1 above except that Dye 2 was used in place of Dye 1.

Inks 3 and 4

These were prepared as described for Ink 1 above except that Dyes 7 and 8 respectively were used in place of Dye 1.

Transfer Sheet TS1

This was prepared by applying Ink 1 to a 6 μm polyester film (substrate) using a wire-wound metal Meyer-bar (K-bar No 2) to produce a wet film of ink on the surface of the sheet. The ink was then dried with hot air to give a 0.54 μm dry film on the surface of the substrate.

Transfer Sheets TS2-TS4

These were prepared as described for TS1 above except that Inks 2-4 respectively were used in place of Ink 1.

Printed Receiver Sheet RS1

A sample of TS 1 was contacted with a transparent receiver sheet of 50 am polyester. The receiver and transfer sheets were placed together on the drum of a transfer printing machine and passed over a matrix of closely-spaced elements which were heated in accordance with a pattern information signal to a temperature of >300° C. for 10 msec, whereby a quantity of the dye, in proportion to the heating period, at the position on the transfer sheet in contact with an element while it was hot was transferred from the transfer sheet to the receiver sheet. After passage over the array of elements the transfer sheet was separated from the receiver sheet. The receiver sheet was laminated with polyester layer before measuring the optical density of the dye on the receiver sheet.

Printed Receiver Sheet RS2-RS4

These were prepared as described for RS1 above except that TS2-TS4 respectively were used in place of TS1.

Evaluation of Inks, Transfer Sheets and Printed Receiver Sheets

The stability of the ink was assessed by visual inspection. An ink was considered to be stable if there was no precipitation over a period of two weeks at ambient temperature.

The quality of the printed impression on the transparent receiver sheet was assessed by measuring the optical density and max values by means of a Perkin Elmer Lambda 5 spectrophotometer. The results of the assessments are shown in Table 1:

TABLE 1

| Receiver Sheet | λ(nm) max | Optical Density (OD) |
| --- | --- | --- |
| RS1 | 774 | 0.55 |
| RS2 | 752 | 0.48 |
| RS3 | 785.6 | 0.39 |
| RS4 | 787.2 | 0.26 |

We claim:

1. A benzofuranone of the Formula (1):

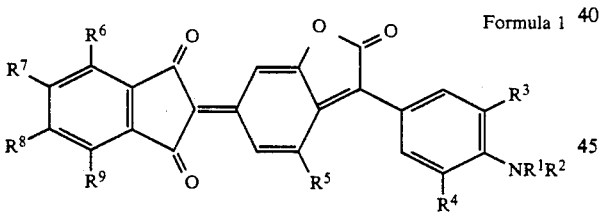

wherein:

$R^1$ and $R^2$ are each independently —H or optionally substituted $C_{1-20}$-alkyl;

$R^3$ and $R^4$ are each independently —H or optionally substituted $C_{1-6}$-alkyl;

$R^5$ is selected from —H, —CN, —COOR$^{10}$ and —COR$^{10}$, in which $R^{10}$ is —H or $C_{1-6}$-alkyl;

$R^6$, $R^7$, $R^8$ and $R^9$ are each independently selected from —H, —NR$^1$R$^2$, —NO$_2$, halogen, optionally substituted $C_{1-6}$-alkyl and optionally substituted $C_{1-6}$-alkoxy, wherein each of the optionally substituted groups $R^1$ to $R^9$ carry substituents selected from the group consisting of phenyl and cyclohexyl.

2. A benzofuranone of the Formula (1):

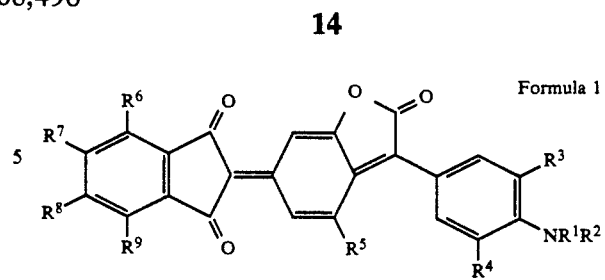

wherein:

$R^1$ and $R^2$ are each independently —H or $C_{1-16}$-alkyl;

$R^3$ and $R^4$ are each independently —H or $C_{1-4}$-alkyl; and $R^5$, $R^6$, $R^7$, $R^8$ and $R^9$ are —H.

3. A process for the preparation of a benzofuranone of Formula (1)

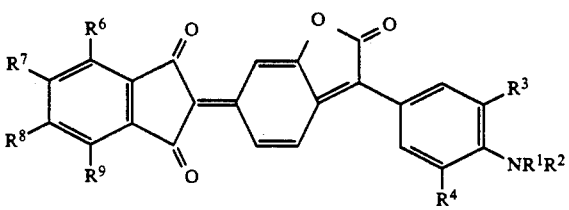

by reacting a compound of the Formula (2):

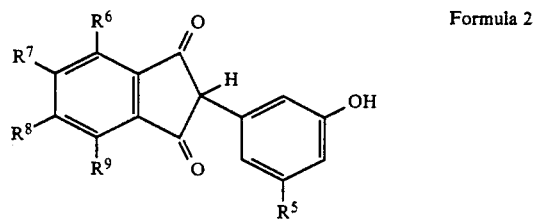

with a compound of the Formula (3):

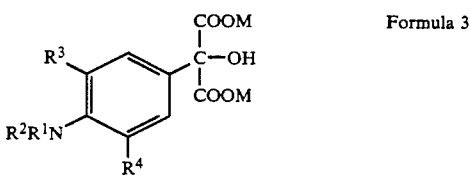

wherein:

$R^1$ and $R^2$ are each independently —H or optionally substituted $C_{1-20}$-alkyl;

$R^3$ and $R^4$ are each independently —H or optionally substituted $C_{1-6}$alkyl;

$R^5$ is selected from —H, —CN, —COOR$^{10}$ and —COR$^{10}$, in which $R^{10}$ is —H or $C_{1-6}$-alkyl;

$R^6$, $R^7$, $R^8$ and $R^9$ are each independently selected from —H, —NR$^1$R$^2$, —NO$_2$, halogen, optionally substituted $C_{1-6}$-alkyl and optionally substituted $C_{1-6}$-alkoxy; and M is —H or metal, wherein each of the optionally substituted groups $R^1$ to $R^9$ carry substituents selected from the group consisting of phenyl and cyclohexyl.

* * * * *